United States Patent [19]

Siegfried et al.

[11] Patent Number: 5,567,472
[45] Date of Patent: Oct. 22, 1996

[54] METHOD AND APPARATUS FOR FORMING A PULSED STREAM OF PARTICLES FOR APPLICATION TO A FIBROUS WEB

[75] Inventors: Robert H. Siegfried; James M. Fleming; Michael J. Stalford, all of Cincinnati; John P. Janson, Cleves, all of Ohio

[73] Assignee: The Procter & Gamble Company, Cincinnati, Ohio

[21] Appl. No.: 440,805

[22] Filed: May 15, 1995

Related U.S. Application Data

[62] Division of Ser. No. 332,022, Oct. 31, 1994.

[51] Int. Cl.$^6$ .............................. B05D 1/02; B05D 1/12; B05B 1/08; B05B 7/14
[52] U.S. Cl. ......................... 427/180; 427/424; 239/101; 239/427.3
[58] Field of Search .................................. 118/300, 325; 427/180, 200, 424; 239/99, 101, 427, 427.3, 427.5, 428

[56] References Cited

U.S. PATENT DOCUMENTS

| | | | |
|---|---|---|---|
| 4,128,667 | 12/1978 | Timson | 427/348 |
| 4,543,274 | 9/1985 | Mulder | 427/197 |
| 4,600,603 | 7/1986 | Mulder | 427/180 |
| 4,715,535 | 12/1987 | Mulder | 239/1 |
| 4,764,325 | 8/1988 | Angstadt | 264/113 |
| 4,765,780 | 8/1988 | Angstadt | 406/123 |
| 4,770,344 | 9/1988 | Kaiser | 239/8 |
| 4,800,102 | 1/1989 | Takada | 427/197 |
| 4,824,295 | 4/1989 | Sharpless | 406/109 |
| 4,888,231 | 12/1989 | Angstadt | 428/213 |
| 4,904,440 | 2/1990 | Angstadt | 264/517 |
| 4,908,175 | 3/1990 | Angstadt | 264/113 |
| 4,927,346 | 5/1990 | Kaiser et al. | 425/81.1 |
| 4,927,582 | 5/1990 | Bryson | 264/113 |
| 5,017,324 | 5/1991 | Kaiser et al. | 264/510 |
| 5,037,247 | 8/1991 | Kaiser et al. | 406/153 |
| 5,093,059 | 3/1992 | Nathoo et al. | 264/121 |
| 5,102,585 | 4/1992 | Pieper et al. | 264/37 |
| 5,156,902 | 10/1992 | Pieper et al. | 428/206 |
| 5,248,524 | 9/1993 | Soderlund | 427/200 |
| 5,279,854 | 1/1994 | Kendall et al. | 427/197 |

FOREIGN PATENT DOCUMENTS

| | | |
|---|---|---|
| WO87/04643 | 8/1987 | European Pat. Off.. |
| 2753268A1 | 11/1977 | Germany. |
| 2002709 | 8/1978 | United Kingdom. |
| WO88/04165 | 6/1988 | WIPO. |

OTHER PUBLICATIONS

Advertisement, "Fox Venturi Eductors for Conveying Solids with No Moving Parts" published by Fox Valve Development Corporation of Dover, NJ 1991.
Fox Venturi Eductors Price List Effective Jan. 1, 1992.
Advertisement, "Series–II Flexi–Spray® Applicator" published by Nordson Corporation Jan. 1988.
General Safety Precautions, Powder Spray Equipment and Systems from Manual No. 30–1. pp. 1–1, 1–2, 1–3, 1–4, 1–5, and 1–6 issued by Nordson Corporation Jan. 1990.
Flexi–Spray® Series II Gun from Manual No. 31–10, pp. 1–23 issued by Nordson Corporation Mar. 1988.

(List continued on next page.)

*Primary Examiner*—Shrive Beck
*Assistant Examiner*—Fred J. Parker
*Attorney, Agent, or Firm*—Gerry S. Gressel; Larry L. Huston; E. Kelly Linman

[57] ABSTRACT

The present invention provides a method and apparatus for forming a pulsed stream of discrete particles of absorbent material. The apparatus comprises a particle metering apparatus for providing a stream of particles having a predetermined mass flow rate, an ejector having an acceleration air nozzle for accelerating the stream of particles, at least one deceleration air nozzle; and valving for alternately directing air through the acceleration and deceleration nozzles. The apparatus can be used to form a fibrous web having a predetermined variation in basis weight of absorbent material along the length of the web.

12 Claims, 5 Drawing Sheets

OTHER PUBLICATIONS

Pump Assembly Information from High Volume Powder Pump Manual No. 32–11. pp. 1–4 issued by Nordson Corporation Mar. 1989.

Section 2, "Equipment Familiarization" from Flexi–Spray® Superabsorbant Manual No. 38–1, pp. 2–1 through 2–23, issued by Nordson Corporation Mar. 1988.

Section 3, "Installation" from Flexi–Spray® Superabsorbant Manual No. 38–1. pp. 3–1 through 3–17, issued by Nordson Corporation Mar. 1988.

METHOD AND APPARATUS FOR FORMING A PULSED STREAM OF PARTICLES FOR APPLICATION TO A FIBROUS WEB

This is a divisional of application Ser. No. 08/332,022, filed on Oct. 31, 1994.

FIELD OF THE INVENTION

This invention is related to a method and apparatus for forming fibrous webs having a predetermined distribution of particulate material. More particularly, the invention is related to forming a pulsed stream of particulate material for application to a fibrous web.

BACKGROUND OF THE INVENTION

Absorbent articles such as disposable diapers, incontinence pads, and catamenial napkins generally include an absorbent core for receiving and holding body exudates. The absorbent core typically includes a fibrous web, which can be a nonwoven, airlaid web of natural or synthetic fibers, or combinations thereof. A class of particulate absorbent materials known as superabsorbent polymers or absorbent gelling materials can be incorporated in the fibrous web to improve the absorption and retention characteristics of the fibrous web.

Because absorbent gelling materials are generally significantly more expensive than readily available natural or synthetic fiber materials (e.g., cellulose fibers), it is advantageous to reduce the quantity of absorbent gelling material in the core. Rather than uniformly reducing such particles throughout the entire core, it is desirable to distribute the particles in the absorbent core in a predetermined manner so that the particles are located where they will be most effective in acquiring and retaining body exudates.

Various techniques have been developed to distribute and locate absorbent materials on or within a fibrous substrate. U.S. Pat. No. 4,800,102 issued to Takada discloses applying a powder to the top surface of a substrate by spraying powder through an opening in a rotating disc. U.S. Pat. No. 4,028,224 issued to Pieper et al. discloses pulsing and diverting mechanisms for producing an intermittent flow of absorbent particles.

U.S. Pat. Nos. 4,543,274 issued Sep. 24, 1985 to Mulder discloses a powder spray gun wherein high velocity air is said to impact powder entrained air contained in the bore of the gun. U.S. Pat. No. 4,600,603 issued Jul. 14, 1986 to Mulder discloses a powder spray gun apparatus wherein an inverted flow amplifier is located adjacent to the inlet of the gun to enhance blending of powder within the gun. From the inverted flow amplifier, the blended powder is supplied to a downstream air flow amplifier which is operable to impact air entrained powder with a high velocity stream of compressed air. A powder control system controls powder supply from powder supply pumps to the spray gun. The powder pumps are said to be conventional venturi powder pumps.

U.S. Pat. No. 4,770,344 issued Sep. 13, 1988 to Kaiser discloses a powder spraying system including a volumetric or gravimetric material feeding device for metering a quantity of powder into a manifold, and air flow amplifiers connected to passageways formed in the manifold. Kaiser '344 teaches that a problem associated with venturi powder pumps is the difficulty in obtaining a consistently accurate feed rate of powder material, especially when a spray gun is operated intermittently. Applicants have also found that the use of venturi powder pumps and associated fluidized bed supply systems is undesirable because of difficulty in controlling powder feed rates, and because such systems can result in poor powder pulse definition. U.S. Pat. Nos. 4,927,346 and 5,017,324 issued to Kaiser disclose additional embodiments for depositing particulate material into a pad with a spray gun, including an embodiment having an inverted flow amplifier and an embodiment having a rotating screw for providing a metered quantity of absorbent particles.

U.S. Pat. No. 5,037,247 issued to Kaiser et al. discloses a powder pumping apparatus having a venturi passageway and an air nozzle including a valve mechanism. Kaiser '247 teaches that it is desirable to include a valve in the air nozzle to eliminate the "dead zone" in the air supply tube extending between the valve and the inlet to the pump body, and thereby eliminate the powder pulse "tailing effect" experienced in other powder pump designs. However, such an arrangement has the disadvantage of a requiring a valve assembly adjacent to or within the nozzle, which may not be practical or even possible in every installation due to space or geometry constraints.

While the above references provide descriptions of particle spraying systems suitable for use in forming absorbent webs, engineers and scientists continue the search for particle depositions systems that provide simple yet precise deposition of absorbent materials in fibrous webs.

Accordingly, it is an object of the present invention to provide an apparatus and method for applying discrete particles to a fibrous web.

It is another object of the present invention to provide a pulse of discrete particles for application to a predetermined location on a fibrous web.

Another object of the present invention is to provide an apparatus for applying powder to a fibrous web, the apparatus comprising a metering apparatus for providing a stream of powder having a predetermined mass flow rate, an acceleration air nozzle for providing a particle accelerating airflow, at least one deceleration air nozzle for providing a particle decelerating airflow, and valving for controlling airflow to the acceleration and deceleration air nozzles.

SUMMARY OF THE INVENTION

The present invention comprises an apparatus for and method of applying discrete particles to a predetermined location on a fibrous web or other absorbent substrate. The apparatus includes a particle metering apparatus for providing a stream of particles having a predetermined mass flow rate, and a particle accelerating apparatus for receiving and accelerating the stream of particles provided by the particle metering apparatus. Metering a supply of particles to provide a stream of particles having a predetermined mass flow rate is advantageous because such metering decouples the amount of absorbent material applied to each web from the formation and shape of a pulse of the particles.

The particle accelerating apparatus includes an acceleration air nozzle for providing a particle accelerating airflow in a downstream direction, a particle outlet disposed downstream of the acceleration air nozzle, and a particle inlet for receiving the stream of particles provided by the particle metering apparatus.

The apparatus further includes at least one deceleration air nozzle disposed downstream of the particle inlet for providing a particle decelerating airflow, at least one pressurized air supply for providing airflow to the acceleration and deceleration air nozzles, and valving for controlling airflow to the acceleration and deceleration air nozzles. The valving is operable to vary the airflow to the acceleration and deceleration nozzles in a predetermined manner, and can provide a pulsed airflow to the deceleration and acceleration air nozzles.

In one embodiment the valving is operable to provide airflow to the acceleration and deceleration nozzles in a predetermined cycle, wherein the valving provides airflow to the acceleration air nozzle while preventing airflow to the deceleration air nozzles during a first portion of the predetermined cycle, and wherein the valving prevents airflow to the acceleration air nozzle while providing airflow to the deceleration air nozzles during a second portion of the predetermined cycle. The valving is preferably operable to bleed air from between the valving and the acceleration air nozzle while preventing airflow to the acceleration air nozzle and while providing airflow to the deceleration nozzles. In one embodiment, the acceleration air nozzle provides a particle accelerating airflow along a first axis generally parallel to a downstream direction, and the particle inlet receives particles along a second axis, the second axis forming an included angle with the first axis of between about 45 degrees and about 135 degrees, and preferably about 90 degrees.

The method according to the present invention comprises the steps of: providing a stream of particles having a predetermined mass flow rate; providing a pulsed particle accelerating airflow in a downstream direction; providing a particle decelerating airflow; impacting the stream of particles with the pulsed particle accelerating airflow at a first location to accelerate the particles in a downstream direction; impacting the stream of particles with the particle decelerating airflow at a second location; and directing the stream of particles to the fibrous web downstream of the first and second locations. The step of providing a particle decelerating airflow can comprise providing a pulsed particle decelerating airflow. In one embodiment a step of controlling the particle accelerating and decelerating airflows in a predetermined cycle can comprise providing the acceleration airflow while preventing the deceleration airflow during a first portion of the cycle; and providing the deceleration airflow while preventing the acceleration airflow during a second portion of the cycle.

A step of providing a pulsed particle accelerating airflow can comprise the steps of intermittently providing flow communication between the air supply and the acceleration air nozzle; intermittently preventing flow communication between the air supply and the acceleration air nozzle; and bleeding air from between the acceleration air valve and the acceleration air nozzle while preventing flow communication between the acceleration air nozzle and the air supply and while providing flow communication between the deceleration air nozzles and the air supply.

BRIEF DESCRIPTION OF THE DRAWINGS

While the specification concludes with claims particularly pointing out and distinctly claiming the present invention, it is believed the present invention will be better understood from the following description in conjunction with the accompanying drawings in which:

DETAILED DESCRIPTION OF THE INVENTION

While the present invention will be described in the context of providing airlaid fibrous webs for use as absorbent cores in disposable absorbent articles such as disposable diapers, the present invention may also be employed to provide absorbent webs for use in a number of other articles, including but not limited to incontinence briefs, disposable training pants, and sanitary napkins.

The term "air" used herein refers to any combinations of gases in which particles can be entrained, including but not limited to atmospheric air.

Figure 1:
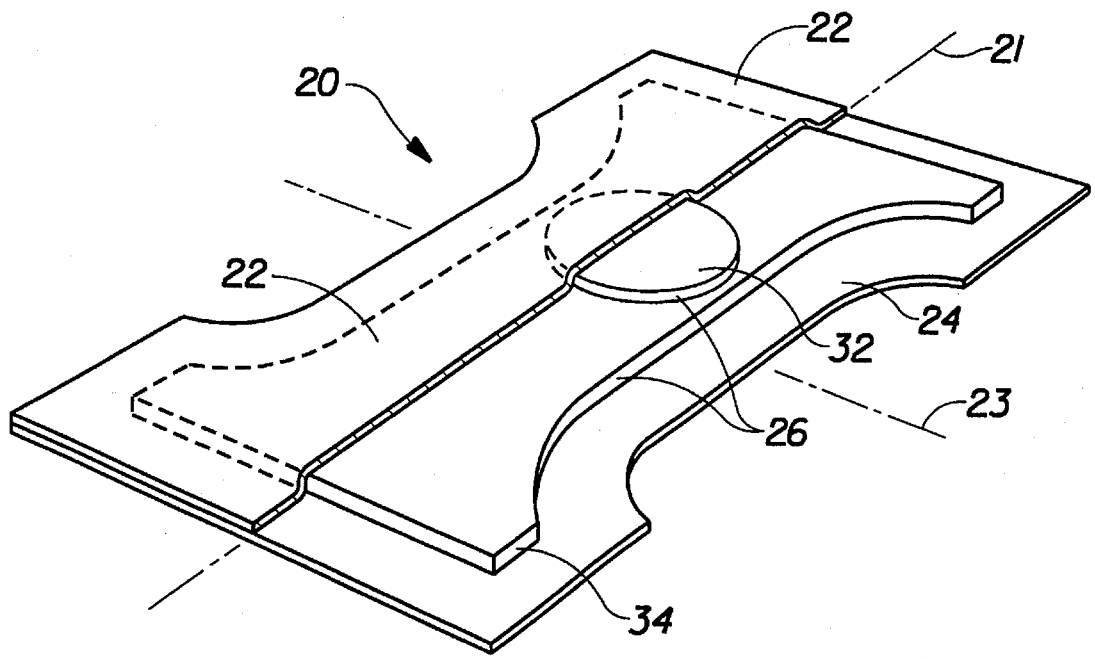
FIG. 1 is a perspective view of an absorbent article shown practically cut-away.

FIG. 1 shows a disposable diaper 20 having a liquid pervious topsheet 22, a liquid impervious backsheet 24, and an absorbent core 26 disposed between the topsheet 22 and the backsheet 24. Preferred constructions of such disposable diapers are described in U.S. Pat. No. 3,860,003 issued Jan. 14, 1975 to Buell and U.S. Pat. No. 5,151,092 issued Sep. 29, 1992 to Buell et al., which patents are incorporated herein by reference. The diaper 20 has a longitudinal centerline 21 and a lateral centerline 23. As used herein, the "longitudinal" dimension, direction, or axis of the diaper 20 is aligned front to back with respect to the wearer as the disposable absorbent article is worn. The "lateral" dimension, direction, or axis of the diaper 20 is perpendicular to the longitudinal direction and is sideways aligned as the diaper is worn.

The absorbent core 26 can include two ore more components, such as a first insert core component 32 and a second shaped core component 34. Preferred absorbent core constructions are described in U.S. Pat. No. 4,673,402 issued Jun. 16, 1987 to Weisman et al.; U.S. Pat. No. 4,685,915 issued Aug. 11, 1987 to Hasse et al.; U.S. Pat. No. 4,834,735 issued May 30, 1989 to Alemany et al.; U.S. Pat. No. 5,217,445 issued Jun. 8, 1993 to Cook et al.; and U.S. Pat. No. 5,234,423 issued Aug. 10, 1993 to Alemany et al.; which patents are incorporated herein by reference. The insert core component 32 serves to collect and distribute discharged body fluid, and can comprise a web of hydrophilic fiber material. The insert core component 32 can be free of particles of absorbent gelling material, or alternatively, can include an amount of particles of such material.

Figure 2:
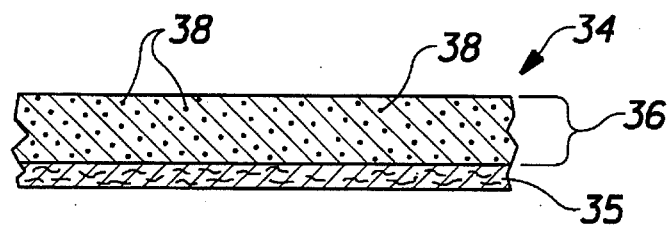
FIG. 2 is a cross-sectional view of an absorbent core having a dusting layer and a layer including discrete particles of absorbent material.

The shaped core component 34 absorbs discharged body fluids from the insert core component 32 and retains such fluids. As shown in FIGS. 1 and 2, the shaped core component 34 includes a thin dusting layer 35 of hydrophilic fiber material overlayed by a primary layer 36 of a combination of hydrophilic fiber material and discrete particles 38 of substantially water insoluble, fluid absorbing, absorbent gelling materials. While the dusting layer 35 is preferably a relatively thin layer of hydrophilic fiber material, it should be understood that the term "dusting layer" denotes a layer of the fibrous web and includes layers having a thickness.

There are several suitable absorbent gelling materials which can be used to form the discrete particles 38 in the shaped core component 34, such as silica gels or organic compounds such as crosslinked polymers. Particularly preferred absorbent gelling materials are hydrolyzed acrylonitrile grafted starch, acrylic acid grafted starch, polyacrylates and isobutylene maleic anhydride copolymers, or mixtures thereof. U.S. Patent Re 32,649 reissued to Brandt et al. Apr. 19, 1988 is incorporated herein by reference for the purpose of showing suitable absorbent gelling materials.

Figure 3:
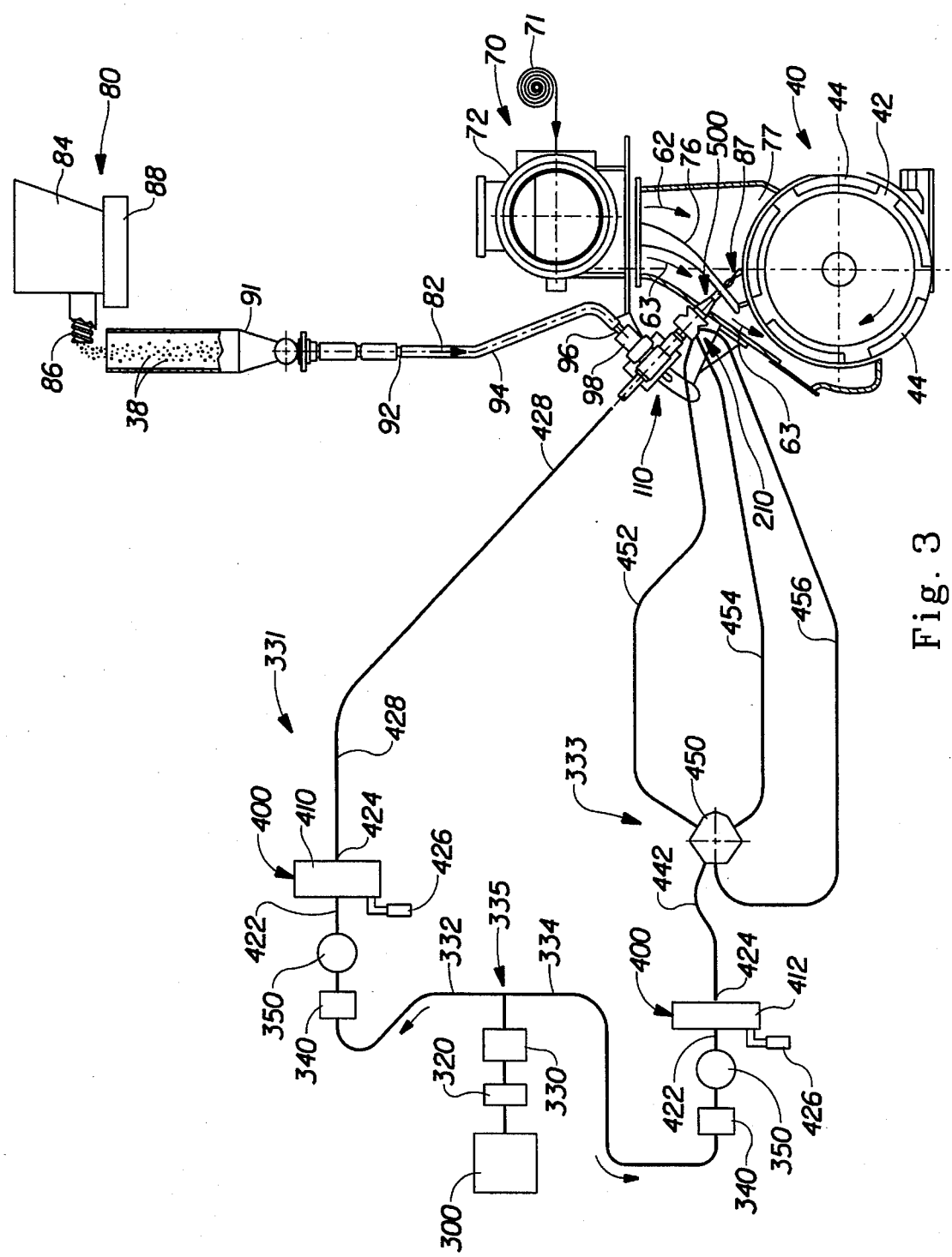
FIG. 3 is a schematic illustration of an apparatus according to one embodiment of the present invention, the illustration showing acceleration air and deceleration air circuits, an airlaying module, and an ejector for directing particles into a forming chamber in the airlaying module.

FIG. 3 shows an apparatus according to the present invention for forming an pulsed stream of absorbent gelling material particles and applying the pulsed stream of materials to a fibrous web. A pulsed stream of particles is a stream of particles having a particle flow rate which is periodically stopped or reduced. The apparatus includes a conveyor for supporting and moving a fibrous web, and preferably comprises an airlaying means such as a rotating drum-type airlaying module 40 having a foraminous forming element, such as a foraminous forming drum 42. Airlaying module 40 is suitable for forming an airlaid fibrous web, such as shaped core component 34. The apparatus also preferably includes a means for forming an air-entrained stream of fibers 62, such as a disintegrator 70.

Figure 4:
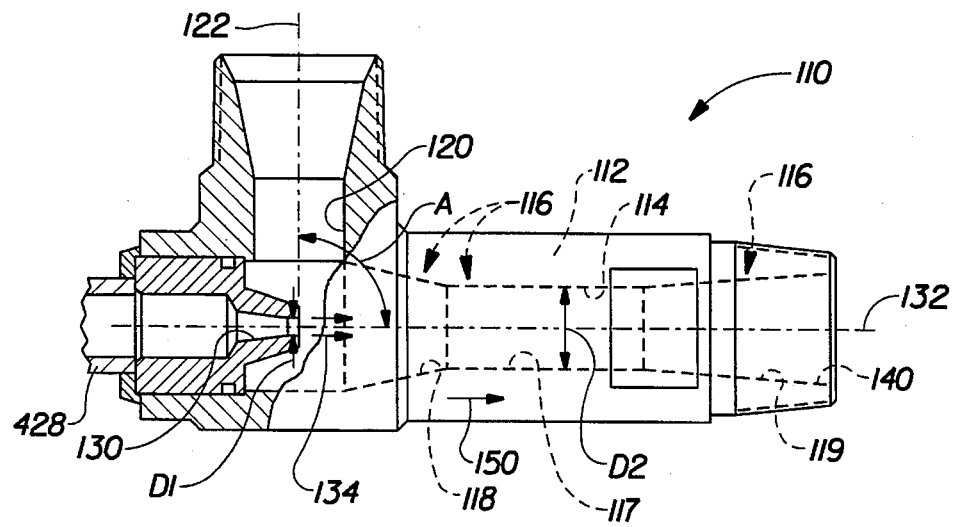
FIG. 4 is a schematic illustration of an ejector suitable for accelerating particles.
Figure 5:
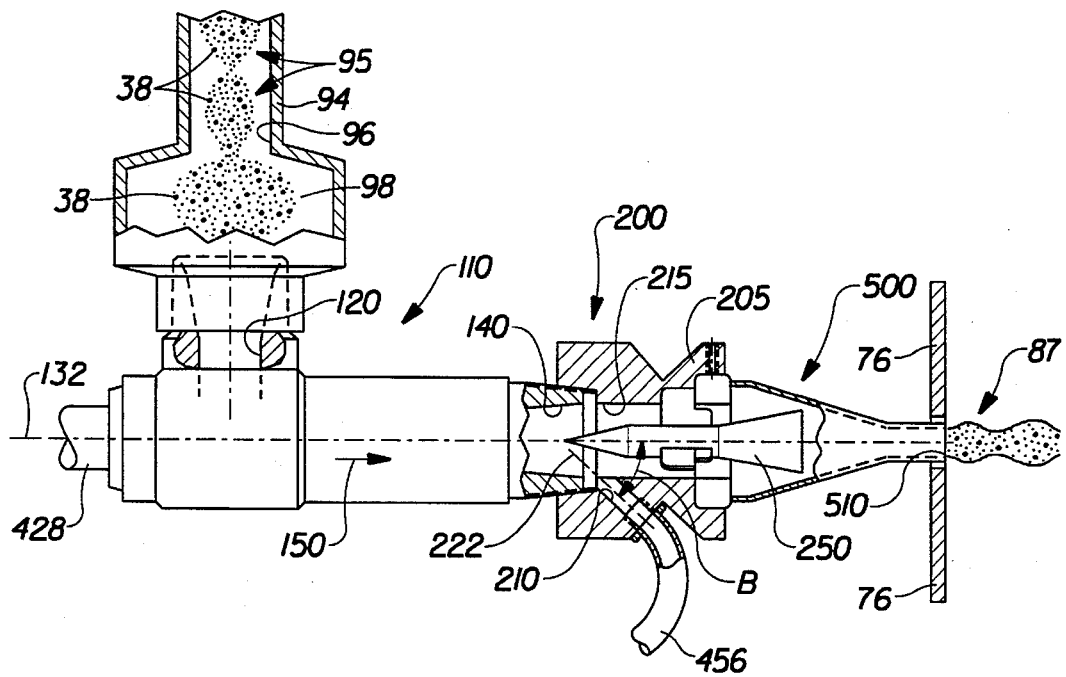
FIG. 5 is a schematic illustration of an ejector having a deceleration nozzle assembly in flow communication with the particle outlet of the ejector, and a particle spreading nozzle extending downstream from the deceleration air nozzle assembly.

Referring to FIGS. 3–5, the apparatus further includes a particle metering apparatus 80 for providing a supply stream 82 of particles 38 having a predetermined mass flow rate, and a particle accelerating apparatus 110. The particle accelerating apparatus 110 has a particle inlet 120 for receiving the stream 82 of particles 38 provided by the particle metering apparatus 80, and an acceleration air nozzle 130 for providing a particle accelerating airflow 134 in a downstream direction 150 shown in FIG. 4. The apparatus further comprises comprises at least one deceleration air nozzle 210 positioned downstream of the particle inlet 120 for providing a particle decelerating airflow, at least one pressurized air supply 300 for providing an airflow to the acceleration nozzle 130 and the deceleration nozzles 210, and valving 400 for controlling airflow to the acceleration and deceleration air nozzles.

Referring to the components in FIG. 3 in more detail, the disentegrator 70 can include a rotary element (not shown) enclosed in a housing 72. The disintegrator 70 receives a fibrous sheet material 71 capable of being separated into individual fibers. The fibrous sheet material 71 can include synthetic and/or natural fibers, and preferably comprises cellulosic fibers. Teeth on the rotary element separate the individual fibers of the sheet material 71 as the sheet material 71 is fed into the disintegrator 70.

A fiber flow splitter 76 separates the stream of air-entrained fibers provided by the disintegrator 70 to separate an air-entrained stream of fibers 62 from a dusting layer air-entrained steam of fibers 63. The stream of fibers 63 forms the dusting layer 35 shown in FIG. 2. The fiber flow splitter 76 also forms a wall which forms part of the boundary of a web forming chamber 77 positioned adjacent the foraminous forming drum 42.

U.S. Pat. Nos. 4,908,175 and 4,765,780, issued Mar. 13, 1990 and Aug. 23, 1988, respectively, to Angstadt et al., are incorporated herein by reference for the purpose of showing the construction of a suitable disintegrator 70 and associated apparatus for providing the air-entrained stream of fibers 62 and the dusting layer air-entrained stream of fibers 63. However, it will be understood by those skilled in the art that other apparatus for separating a roll or mat of fibrous material into individual fibers, including but not limited to hammermills, fiberizers, picker rolls, and likerin rolls, may be used to provide the air-entrained streams of fibers 62 and 63.

The airlaying module 40 includes the rotating foraminous forming drum 42 on which fibrous webs can be formed. The foraminous forming drum 42 can include a plurality of formation cavities 44 circumferentially spaced about the periphery of the forming drum 42. Five formation cavities 44 are shown in FIG. 3, with each formation cavity 44 having a circumferential span of about seventy-two degrees. The forming drum 42 is rotated by a motor (not shown) or other suitable device. The forming drum 42 rotates in the direction shown in FIG. 3 such that fibers in the dusting layer air-entrained stream of fibers 63 are first deposited in the formation cavities 44 to form the dusting layer 35 shown in FIG. 2. The stream of fibers 62 is then deposited in cavities 44 to overlay the dusting layer.

The airlaying module 40 includes a plurality of vacuum chambers (not shown) within the interior of the foraminous forming drum 42. Each of the vacuum chambers is connected to a suitable source of vacuum (not shown). Entrainment air for forming air-entrained streams of fibers 62 and 63 is drawn through the foraminous forming drum 42 by the vacuum maintained in the vacuum chambers within the interior of the forming drum 42. U.S. Pat. No. 4,592,708 issued Jun. 3, 1986 to Feist et al. and above referenced U.S. Pat. Nos. 4,908,175 and 4,765,780 are incorporated herein by reference for the purpose of showing a suitable airlaying module 40 for use with the present invention.

As the stream of fibers 62 is deposited in the cavities 44, the particle accelerating apparatus 110 and decelerating air nozzles 210 provide a pulsed stream 87 of absorbent particles 38 which are directed by a particle distributing nozzle 500 through an opening in the fiber flow splitter 76. The pulsed stream 87 of particles 38 enter the forming chamber 77 and mix with the fiber stream 62 as the fiber stream 62 is deposited in the formation cavities 44. Accordingly, the webs formed in the cavities 44 have a basis weight of absorbent particles 38 which varies along the longitudinal axis of the web.

The particle metering apparatus 80 provides a stream 82 of particles 38 having a predetermined mass flow rate. The particle metering apparatus 80 provides a mass flow rate of particles 38 which is independent of the manner in which the pulsed stream 87 of particles 38 is formed and shaped. Accordingly, the formation and shape of the pulsed stream 87 can be controlled and varied with the acceleration and deceleration airflows without detrimentally affecting the amount of particles 38 incorporated in each web formed on the foraminous forming drum 42. The metering apparatus 80 can include a hopper 84, screw feeder 86, and scale 88. A suitable metering apparatus 80 is an Acrison Volumetric Feeder, Model No. 405-105X-F, available from Acrison, Inc. of Moonachie, N.J. The metering apparatus 80 is operated to provide a mass flow rate of about 0.02 to about 0.5 pounds per second, and more preferably between about 0.13 and about 0.26 pounds per second of particles 38.

The stream 82 of metered particles 38 is delivered by screw feeder 86 to a funnel receiver 91 and directed to the inlet 92 of a particle delivery conduit 94. The conduit 94 has a length at least five times its internal diameter. The conduit 94 can have an inner diameter of about 1 inch, and a length of at least about sic inches, more preferably at least about 20 inches, and most preferably between about 30 inches to about 120 inches. The conduit 94 carries the stream 82 of metered particles 38 intermediate the particle metering apparatus 80 and the particle accelerating apparatus 110. The conduit 94 has an outlet 96 (FIG. 5) in flow communication with a particle storage chamber 98. The storage chamber 98 has an internal diameter greater than that of conduit 94. The storage chamber can have an inner diameter of at least about 1.75 inches and a volume of about 6 cubic inches. The storage chamber 98 is disposed intermediate the outlet 96 and the particle inlet 120 of the particle accelerating apparatus 110, as shown in FIGS. 3 and 4. The storage chamber 98 provides for accumulation of particles 38 upstream of the acceleration air nozzle 130 when airflow to the acceleration air nozzle 130 is prevented and particle decelerating airflow is directed through the deceleration nozzles 210. Without being limited by theory, it is believed the chamber 98 aids in maintaining movement of the particles 38 at the exit of the conduit 94, and helps disperse the particles at the exit of the conduit 94, thereby preventing excessive concentrations of particles in any longitudinal region of the fibrous web.

Referring to FIGS. 4 and 5, the particle accelerating apparatus 110 can comprise an ejector having a main barrel portion 112 having a bore 114, the bore 114 extending along a first axis 132 from the acceleration air nozzle 130 to the particle outlet 140. The diameter D1 of the acceleration air nozzle 130 is smaller than the minimum diameter D2 of the bore 114. The diameters D1 and D2 can be about 0.20–0.25 inch and about 0.825 inch, respectively. The acceleration air nozzle 130 provides the particle accelerating airflow 134 along the first axis 132, and the particle inlet 120 receives and directs particles 38 into the bore 114 along a second axis 122. The second axis 122 preferably forms an included angle A with the first axis 132 of between about 45 degrees and about 135 degrees, and more preferably about 90 degrees, so that the particle accelerating airflow 134 provided by the acceleration nozzle 130 is the primary source of downstream acceleration imparted to the particles 38.

The bore 114 can include a venturi passageway 116 disposed downstream of the acceleration air nozzle 130 and the particle inlet 120. The venturi passageway 116 extends along the first axis 132 and includes a converging passageway portion 118, a diverging passageway portion 119 disposed downstream of the converging passageway portion 118, and a throat portion 117 extending intermediate the converging passageway 118 and the diverging passageway 119. A suitable ejector for use as a particle accelerating apparatus 110 is a Fox Eductor, 1-½ inch Series 300-SCE, having a number 613937 nozzle and a number 613763 body, manufactured by the Fox Valve Development Corporation, of Dover, N.J.

The static pressure of the particle accelerating airflow decreases as the particle accelerating airflow 134 passes through the converging passageway portion 118. The reduction of static pressure in the bore 114 helps to draw particles 38 into the bore 114 through the particle inlet 120. Accordingly, pulsing of the particle accelerating airflow 134 causes a varying suction pressure within the bore 114. Without being limited by theory, it is believed that this varying suction pressure, in turn, establishes a standing wave 95 (FIG. 5) of varying particle concentration and phasing within the particle delivery conduit 94.

FIG. 5 shows a standing wave 95 having three pulses of particles adjacent the exit of the conduit 94 and the chamber 98, but it will be understood that the pulses can occur along the entire length of the conduit 94. Phasing of the particles 38 within the conduit 94 is believed to enhance formation of well defined pulses of particles 38 in the pulsed stream 87. Because there are several pulses in the conduit 94 at any given time, a pulse of particles does not need to travel the entire length of the conduit 94 in the time interval associated with a product cycle (one fifth rotation of the drum 42). Accordingly, the rate of acceleration of the particles 38 provided by the particle accelerating apparatus 110 can be set independent of the rotational speed of the drum 42. The throat portion 117 of the venturi passageway 116 focuses the particles 38 accelerated by the particle accelerating airflow 134, so that the particles can be spread mechanically at a downstream location.

A deceleration air nozzle assembly 200 is joined to the particle acceleration apparatus 110. The deceleration air nozzle assembly 200 has a body portion 205 having a central bore 215 extending along the axis 132 downstream of the particle outlet 140. The central bore 215 is in flow communication with the particle outlet 140 of the particle accelerating apparatus 110, and can have a diameter of about 1.5 inches. The decelerating air nozzle assembly 200 includes at least one deceleration air nozzle 210 for providing a particle decelerating airflow having a velocity component in an upstream direction opposite to direction 150. In FIG. 5 only one deceleration air nozzle 210 is shown, though it will be understood that the deceleration air nozzle assembly 200 includes three deceleration air nozzles 210 circumferentially spaced around the body portion 205 at equal angular intervals of about 120 degrees. Each nozzle 210 can have an inner diameter of about ⅜ inch. Each nozzle 210 directs a particle decelerating airflow along an axis 222 forming an included angle B with the first axis 132. The angle B can be between 0 degrees and about 85 degrees, and in the embodiment shown is about 45 degrees.

A particle spreader 250 is supported in the bore 214 to extend along axis 132. The particle spreader 250 spreads the particles 38 focused by the throat 117 in a radial direction in the plane of FIG. 5. The particle distributing nozzle 500 extends downstream of the deceleration air nozzle assembly 200 and directs the pulsed stream 87 through an opening in the fiber flow splitter 76. The particle distributing nozzle 500 transitions from an upstream circular shape to a downstream rectangular shape to spread the particles 38 in a direction perpendicular to the plane of FIG. 5. The nozzle 500 can have an upstream inner diameter of about 1.5 to 2 inches and a downstream exit 510 having a width in the plane of FIG. 5 of about 0.5 to about 0.7 inches and a width perpendicular to the plane of FIG. 5 of about 3.0 inches.

AIR CIRCUIT AND VALVING

Pressurized air is supplied to the acceleration air nozzle 130 and the deceleration air nozzles 210 by the air supply circuit shown in FIG. 3. The air supply circuit includes a pressurized air supply 300. The air supply 300 can comprise an air compressor and supply tank capable of for providing an airflow of 100 standard (1 atmosphere, 70 degrees F.) cubic feet per minute (SCFM) at a pressure of 100 psi gage. Pressurized air from the supply 300 is directed through a water trap 320 and a flow meter 330 to a splitting tee 335, at which point the pressurized air is directed into separate acceleration and deceleration air circuits through separate acceleration air and deceleration air lines 332 and 334, respectively. Acceleration and deceleration air lines 332 and 334 can have an inner diameter of about ⅝ inch. In FIG. 3 only one air supply 300 is shown, but it will be understood that separate air supplies 300 could be used to feed each of the air lines 332 and 334 if desired.

The acceleration air circuit is indicated by reference number 331 in FIG. 3, and the deceleration air circuit is indicated by reference number 333. The acceleration air circuit 331 and the deceleration air circuit 33 each include a pressure regulator 340 and an accumulator 350. The pressure regulators 340 can have a pressure range between about 0 and about 80 psi gage, and a flow rate of between 0 and about 70 SCFM. A suitable pressure regulator 340 is a model R17-600 RGLA manufactured by the Norgren Company of Littleton, Col. The accumulators have a volume of about 80 cubic inches. A suitable accumulator 350 is a model 225000 manufactured by the Bendix Company.

The acceleration and deceleration air circuit 331 and 333 including valving 400 for controlling airflow to the acceleration air nozzle 130 and the deceleration air nozzles 210. The valving 400 can comprise a solenoid operated acceleration air valve 410 disposed intermediate the accumulator 350 and the air nozzle 130 in the acceleration air circuit 331, and a solenoid operated deceleration air valve 412 disposed intermediate the accumulator 350 and a manifold 450 in the deceleration air circuit 333. Each of the valves 410 and 412 can include an inlet 422 for receiving airflow from the air supply 300, an outlet 424, and an exhaust port 426 having a variable area exhaust orifice 427. Suitable solenoid operated air valves 410 and 412 are Model 6513B-622-PM-871DA-M599/0210 valves manufactured by MAC valve, Inc. of Wixom, Mich.

The outlet 424 of the acceleration air valve 410 is in flow communication with the acceleration air nozzle 130 through an acceleration air nozzle supply line 428. The supply line 428 can have an inner diameter of about ⅝ inch, and a maximum length of about 28 inches. The outlet 424 of the deceleration air valve 412 is in flow communication with the deceleration air nozzles 210 through a manifold supply line 442, the manifold 450, and three deceleration air nozzle supply lines 452, 454, and 456. Deceleration air passing out of the outlet 424 of valve 412 and through the manifold supply line 442 is directed into the supply lines 452, 454, and 456 by the manifold 450. Each of the supply lines 452, 454, and 4568 supplies deceleration air to one of the three deceleration air nozzles 210 in the deceleration air nozzle assembly 200. One of the supply lines, supply line 456, is shown in FIG. 5. The manifold supply line 442 can have an inner diameter of about ⅝ inch, and a maximum length of about 18 inches. The deceleration air nozzle supply lines 452, 454, and 456 can each have an inner diameter of about ¼ and a maximum length of about 10 inches.

The valving 400 is operable to vary the airflow to the acceleration and deceleration air nozzles in a predetermined manner. Preferably, the valving 400 is operable to provide a pulsed airflow to the acceleration air nozzle 130, and a pulsed airflow to the deceleration air nozzles 210. More particularly, the valving 400 can be operable to provide airflow to the acceleration and deceleration nozzles 130 and 210 in a predetermined cycle, wherein the valving 400 provides airflow to the acceleration air nozzle 130 while preventing airflow to the deceleration air nozzles 210 during a first portion of the predetermined cycle, and wherein the valving 400 prevents airflow to the acceleration air nozzle 130 while providing airflow to the deceleration air nozzles 210 during a second portion of the predetermined cycle. The valving 400 can also be operable to provide airflow to both the acceleration air valve 130 and the deceleration air valves 210 during a third portion of the predetermined cycle.

Figure 6:
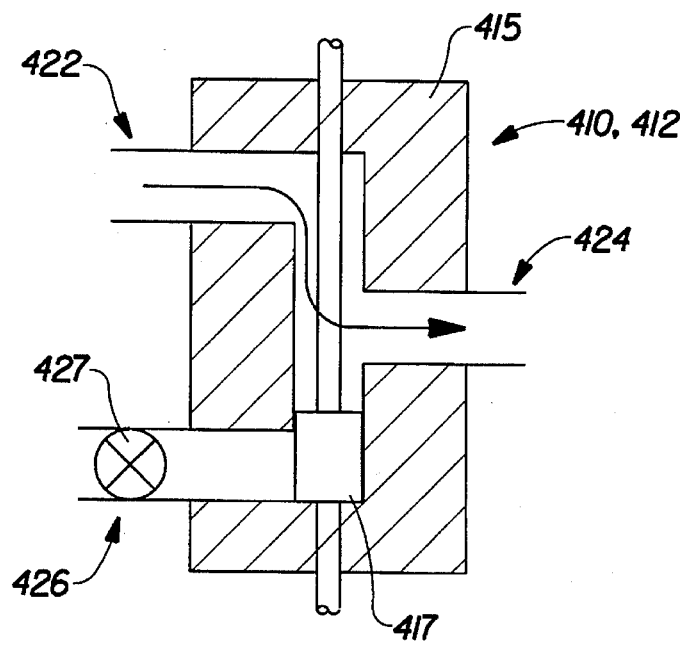
FIG. 6 is a schematic illustration of a valve positioned to provide airflow from the valve inlet to the valve outlet, and positioned to prevent airflow through the exhaust port.
Figure 7:
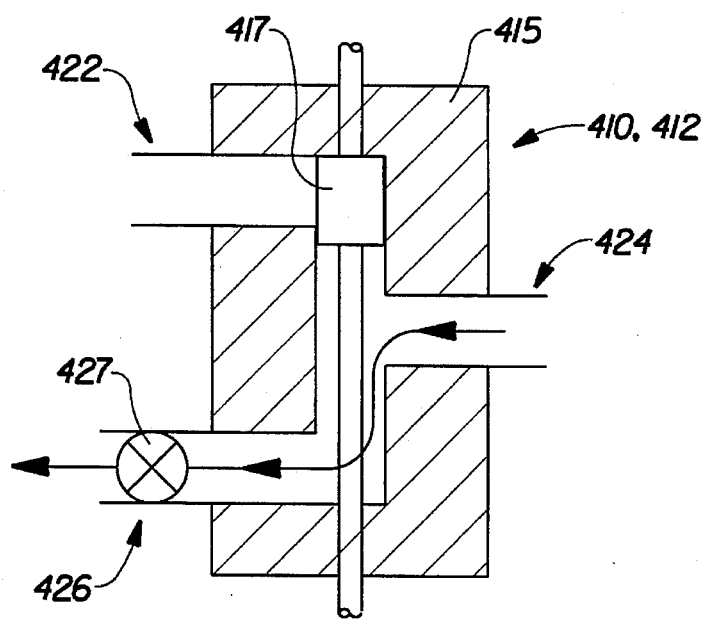
FIG. 7 is a schematic illustration of a valve positioned to prevent airflow from the valve inlet to the valve outlet while permitting venting of air from the outlet through the exhaust port.

FIGS. 6 and 7 are simplified schematic illustrations of the operation of the valve 410, or alternatively, the valve 412. The valve 410 has a valve body 415 in which a movable seal member 417 is disposed. The valve 410 is operable from a first position, shown in FIG. 6 wherein the seal member 417 is positioned to provide flow communication between the inlet 422 and the outlet 424 while preventing flow through the exhaust port 427, to a second position, shown in FIG. 7, wherein the seal member 417 is positioned to provide flow communication between the outlet 424 and the exhaust port 426 while preventing flow from the inlet 422 to the outlet 424.

When the valve 410 is in the first position shown in FIG. 6, the valve provides airflow to the acceleration air nozzle 130. When the valve 410 is in the second position shown in FIG. 7, the valve prevents airflow to the acceleration air nozzle 130 and provides flow communication between the outlet 424 and the exhaust port 426 to bleed air between the valve 410 and the acceleration air nozzle 130 in supply line 428. Such bleeding is desirable to provide a sharp air pulse through the acceleration air nozzle 130. Air pressure remaining in the supply line 428 after the valve has been set to the second position can result in a powder pulse "tail" effect wherein the powder pulses in the pulsed stream 87 take on an elongated tear-drop shape. Bleeding the air between the valve 410 and the acceleration air nozzle 130 when the valve 410 is in the second position provides accurate control of the shape of the powder pulses in pulsed stream 87.

The valve 412 is also operable in the first and second positions shown in FIGS. 6 and 7. When the valve 412 is in the first position shown in FIG. 6, the valve 412 provides airflow from the supply 300 to the deceleration air nozzles 210 via the manifold supply line 442, manifold 450, and deceleration air nozzle supply lines 452, 454, and 456. When the valve 412 is in the second position shown in FIG. 7, the valve prevents airflow to the to the deceleration air nozzles 210 and bleeds air between the valve 412 and the deceleration air nozzles 210 through the exhaust port 426. Bleeding the air between the valve 412 and the deceleration nozzles 210 also helps provide accurate control of the shape of the powder pulses in the pulsed stream 87.

Figure 8:
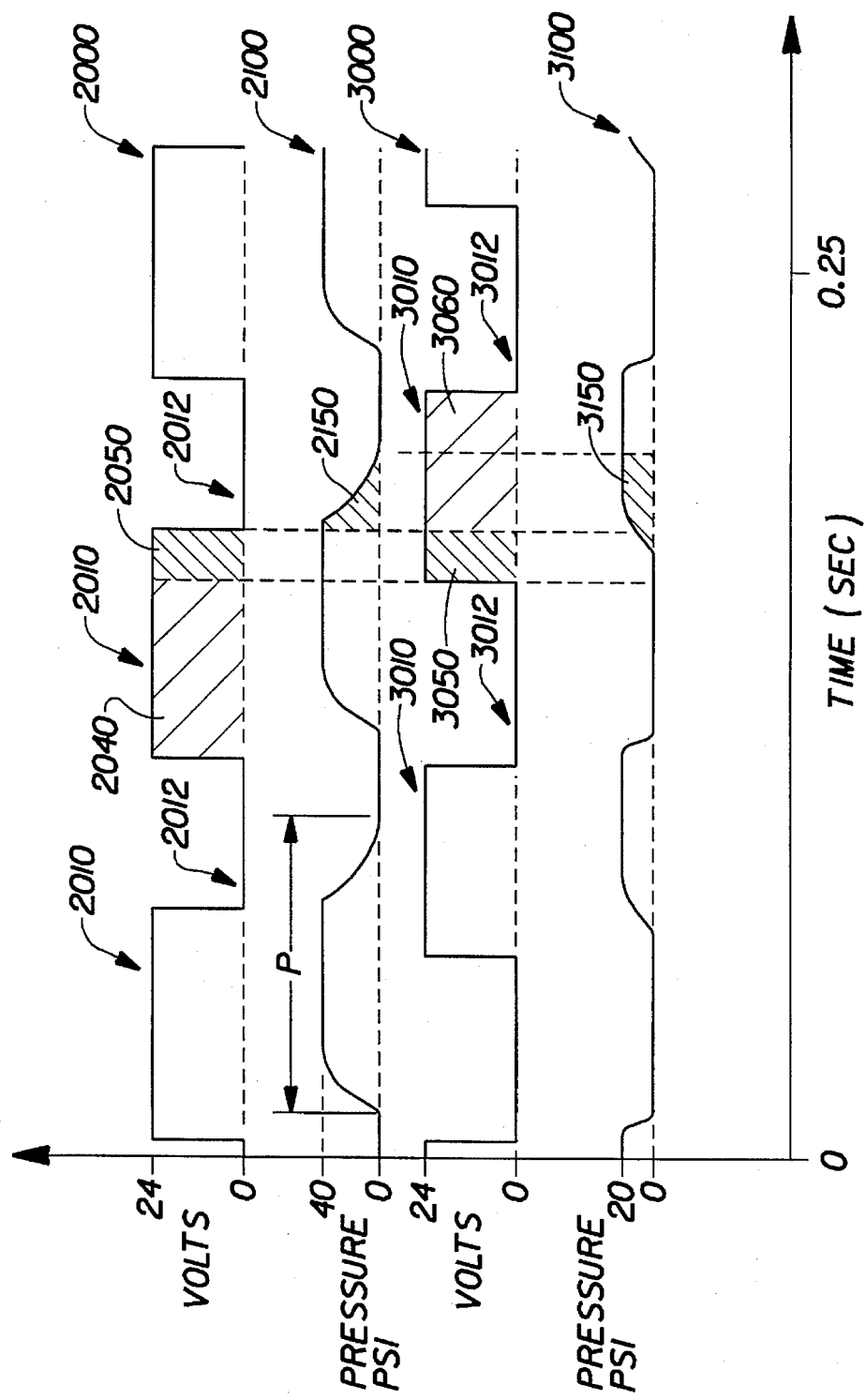
FIG. 8 is a schematic illustration showing the cyclic operation of the acceleration and deceleration air valves showing the acceleration air valve position versus time, corresponding air pressure versus time, the deceleration air valve position versus time, and the corresponding air pressure versus time.

In a preferred embodiment, the valves 410 and 412 are independently operable, such that the valve 410 can be positioned to provide airflow to acceleration air nozzle 130 in a predetermined cycle that can be in or out of phase with the cycle in which valve 412 provides airflow to the deceleration air nozzles 210. The graph in FIG. 8 illustrates operation of the valves 410 and 412 to provide airflow to the acceleration air nozzle 130 and the deceleration air nozzles 210 in a predetermined cycle. Position along the horizontal axis in FIG. 8 represents time in seconds. Curve 2000 in FIG. 8 represents the voltage (as a function of time) applied to the solenoid controlling the position of acceleration air valve 410. The peaks 2010 of curve 2000 correspond to the first position of the valve 410 shown in FIG. 6. The troughs 2012 of curve 2000 correspond to the second position of the valve 410 shown in FIG. 7. Similarly, curve 3000 in FIG. 8 represents the voltage (as a function of time) applied to the solenoid controlling the position of deceleration air valve 412. The peaks 3010 of curve 3000 correspond to the valve 412 being in the first position shown in FIG. 6, and the troughs 3012 correspond to the valve 412 being in the second position shown in FIG. 7. During a first part of a predetermined valve position cycle, indicated by shaded area 2040, valve 410 is in the first position while valve 412 is in the second position shown in FIG. 7. During a second part of the predetermined cycle, indicated by shaded area 3060, valve 410 is in the second position while valve 412 is in the first position shown in FIG. 6. During a third part of the predetermined cycle, indicated by the shaded areas 2050 and 3050, both the valves 410 and 412 are in the first position shown in FIG. 6.

Curve 2100 in FIG. 8 represents the pressure (as a function of time) in acceleration air nozzle supply line 428 adjacent to the acceleration air nozzle 130. The interval P shown adjacent to curve 2100 represents the duration of time corresponding to one pad formed in a cavity 44 of the rotating foraminous forming drum 42. Curve 3100 in FIG. 8 represents the pressure (as a function of time) in the manifold 450 supplying air to the deceleration air nozzles 210. Curves 2100 and 3100 show that: during a first portion of a predetermined airflow cycle, an airflow is provided to the acceleration air nozzle 130 while airflow to the deceleration airflow nozzles 210 is prevented; during a second portion of the predetermined cycle, airflow to the acceleration air nozzle 130 is prevented while airflow is provided to the deceleration air nozzles 210; and during a third portion of the predetermined cycle indicated by shaded areas 2150 and 3150, airflow is provided to both the acceleration air nozzle 130 and the deceleration air nozzles 210. This overlap in airflow to both the acceleration air nozzle 130 and the deceleration air nozzles 210 during the third portion of the cycle helps to keep the particles 38 in constant motion. In addition, it is believed that this overlap gives the deceleration air a "headstart" which helps to provide sharp pulses in the pulsed stream 87. Such sharp pulses provide a sharp longitudinal transition from a relatively high basis weight particle distribution in a first portion of the fibrous web to a relatively low particle basis weight distribution in a second portion of the fibrous web.

Sharpness of the pulses in the pulsed stream 87 can be varied in other ways besides overlapping the timing of the airflow to the acceleration and deceleration air nozzles. For instance, varying the orifice size of the exhaust port 426 varies the length of the "tail" of each pulse. By increasing the orifice size of the exhaust port 426, the "tail" of a pulse can be shortened. In addition, the "tail" of each pulse can be shortened by increasing the deceleration air pressure relative to the acceleration air pressure.

While one valving arrangement has been disclosed, it will be understood that other valve types or valve arrangement can be used in accordance with the present invention. For example, in the embodiment shown in FIG. 3, the acceleration and deceleration air valves 410 and 412 are separate, independently operable valves. In an alternative embodiment a single valve could be used. For instance, a valve having a single inlet and two outlets could be used, with one outlet joined to conduit 428 and the other outlet joined to conduit 442, such that when the valve is in a first position airflow is provided to the acceleration air nozzle 130 but not to the deceleration air nozzles 210, and such that when the valve is in a second position airflow is provided to the deceleration air valves 210 but not to the acceleration air valve 130.

The operation of the valves 410 and 412 can be phased with rotation of the forming drum 42 in any suitable manner. For instance, the operation of valves 410 and 412 can be phased with rotation of the forming drum 42 by use of a programmable limit switch. A suitable programmable limit switch is a GEMCO Quick-Set III manufactured by GEMCO of Clawson, Mich. and having a rotational position measurement device and a programmable control module.

The rotational position measuring device can be mechanically coupled to the forming drum 42 such that the rotational position measuring device rotates n times per revolution of the drum 42, where n is the number of fibrous webs formed on the drum circumference (n=5 in FIG. 3). The programmable control module divides each revolution of the rotational position measurement device into 1000 increments. The programmable control module also contains an output channel capable of applying an energizing voltage to each of the valve solenoids. The user can select at which predetermined positions (which increment number between 0 and 1000) each valve solenoid is energized and de-energized, by entering the predetermined positions into the programmable control module.

While particular embodiments of the present invention have been illustrated and described, it would be obvious to those skilled in the art that various changes and modifications can be made without departing from the spirit and scope of the invention. It is intended to cover, in the appended claims, all such modifications and intended uses.

What is claimed is:

1. A method for forming a pulsed stream of discrete particles for application to a fibrous web, the method comprising the steps of:

providing a stream of particles having a predetermined mass flow rate;

providing a pulsed particle accelerating airflow in a downstream direction from a first location to a second location;

providing a particle decelerating airflow;

impacting the stream of particles with the pulsed particle accelerating airflow at the first location to accelerate the particles in the downstream direction to provide a pulsed stream of discrete particles;

impacting the pulsed stream of discrete particles with the particle decelerating airflow at the second location downstream of the first location; and directing the pulsed stream of discrete particles to the fibrous web downstream of the first and second positions.

2. The method of claim 1 wherein the step of providing a particle decelerating airflow comprises the step of providing a pulsed particle decelerating airflow.

3. The method of claim 2 further comprising the step of controlling the particle accelerating and decelerating airflows in a predetermined cycle, wherein the step of controlling the airflows comprises:

providing the acceleration airflow while preventing the deceleration airflow during a first portion of the cycle; and providing the deceleration airflow while preventing the acceleration airflow during a second portion of the cycle.

4. The method of claim 3 wherein the step of controlling the airflows comprises providing both the acceleration airflow and the deceleration airflow during a third portion of the cycle.

5. The method of claim 1 wherein the step of providing a pulsed particle accelerating airflow comprises the steps of:

provliding an air supply;

providing an acceleration air nozzle for directing the pulsed particle accelerating airflow to impact with the stream of particles;

intermittently providing flow communication between the air supply and the acceleration air nozzle;

intermittently preventing flow communication between the air supply and the acceleration air nozzle; and bleeding air from between the acceleration air valve and the acceleration air nozzle while preventing flow communication between the acceleration air nozzle and the air supply.

6. The method of claim 1 wherein the step of impacting the stream of particles comprises:

providing the pulsed particle accelerating airflow along a first axis generally parallel to the downstream direction; and directing the stream of particles along a second axis, the second axis forming an included angle with the first axis of about 90 degrees.

7. The method of claim 1 comprising the step of forming a wave of varying particle concentration in the stream of particles having a predetermined mass flow rate prior to impacting the stream of particles with the pulsed particle accelerating airflow.

8. The method of claim 1 wherein the step of bleeding air from between the acceleration air valve and the acceleration air nozzle comprises the steps of:

providing an exhaust port having a variable orifice size for bleeding air from between the acceleration air valve and the acceleration air nozzle; and varying the exhaust part orifice size to change the shape of the pulsed stream of discrete particles.

9. A method for forming a pulsed stream of discrete particles for application to a fibrous web, the method comprising the steps of:

providing a forming chamber having a foraminous forming member;

providing a flow of fibers to the foraminous forming member to form the fibrous web;

providing a stream of particles having a predetermined mass flow rate;

providing a pulsed particle accelerating airflow;

providing a particle decelerating airflow;

impacting the stream of particles with the pulsed particle accelerating airflow to provide a pulsed stream of discrete particles;

impacting the pulsed stream of discrete particles with the particle decelerating airflow after impacting the stream of particles with the pulsed particle accelerating airflow; and directing the pulsed stream of discrete particles into the forming chamber for application to the fibrous web after impacting the pulsed stream of discrete particles with the particle decelerating airflow.

10. The method of claim 9 wherein the step of providing a particle decelerating airflow comprises the step of providing a pulsed particle decelerating airflow.

11. The method of claim 10 further comprising the step of controlling the particle accelerating and decelerating airflows in a predetermined cycle, wherein the step of controlling the airflows comprises:

providing the acceleration airflow while preventing the deceleration airflow during a first portion of the cycle; and providing the deceleration airflow while preventing the acceleration airflow during a second portion of the cycle.

12. The method of claim 11 wherein the step of controlling the airflows comprises providing both the acceleration airflow and the deceleration airflow during a third portion of the cycle.

* * * * *

UNITED STATES PATENT AND TRADEMARK OFFICE
CERTIFICATE OF CORRECTION

PATENT NO. : 5,567,472
DATED : October 22, 1996
INVENTOR(S) : Robert H. Siegfried et al.

It is certified that error appears in the above-indentified patent and that said Letters Patent is hereby corrected as shown below:

| | |
|---|---|
| Column 3, line 64 | delete "practically" and insert --partially--. |
| Column 4, line 57 | delete "ore" and insert --or--. |
| Column 5, line 15 | delete "a" and insert --any--. |
| Column 5, line 50 | delete "comprises" first occurances. |
| Column 5, line 58 | delete "disentegrator" and insert --disintegrator--. |
| Column 6, line 16 | delete "likerin" and insert --lickerin--. |
| Column 8, line 46 | delete "214" and insert --215--. |
| Column 9, line 17 | delete "33" and insert --333--. |
| Column 9, line 38 | delete "valve" and insert --Valve--. |
| Column 9, line 52 | delete "4568" and insert --456--. |
| Column 13, line 36 | delete "part" and insert --port--. |

Signed and Sealed this

Tenth Day of June, 1997

Attest:

BRUCE LEHMAN

Attesting Officer

Commissioner of Patents and Trademarks